(12) United States Patent
Park et al.

(10) Patent No.: US 8,518,712 B2
(45) Date of Patent: Aug. 27, 2013

(54) METHOD FOR DISCOVERING PHARMACOLOGICALLY ACTIVE SUBSTANCE OF NATURAL PRODUCTS USING HIGH RESOLUTION MASS SPECTROMETRY AND PHARMACOLOGICAL ACTIVITY TEST

(75) Inventors: Kyu Hwan Park, Daejeon (KR); Hyun Sik Kim, Daejeon (KR); Kyung Hoon Kwon, Daejeon (KR); Jong Shin Yoo, Daejeon (KR)

(73) Assignee: Korea Basic Science Institute (KR)

( * ) Notice: Subject to any disclaimer, the term of this patent is extended or adjusted under 35 U.S.C. 154(b) by 0 days.

(21) Appl. No.: 13/538,273

(22) Filed: Jun. 29, 2012

(65) Prior Publication Data
US 2012/0322160 A1 Dec. 20, 2012

Related U.S. Application Data

(63) Continuation of application No. PCT/KR2010/008988, filed on Dec. 15, 2010.

(30) Foreign Application Priority Data

Dec. 29, 2009 (KR) .................. 10-2009-0133083

(51) Int. Cl.
*G01N 27/62* (2006.01)
(52) U.S. Cl.
USPC ............ 436/173; 436/63; 436/161; 436/174; 436/177; 250/282; 702/19; 702/23; 702/27; 702/32; 435/29; 435/32
(58) Field of Classification Search
USPC ................... 436/63, 161, 162, 173, 174, 177; 250/281, 282; 702/19, 22, 23, 25, 27, 30, 702/32; 435/4, 29, 32, 34, 39
See application file for complete search history.

(56) References Cited

U.S. PATENT DOCUMENTS

| | | | |
|---|---|---|---|
| 6,579,720 B1 * | 6/2003 | Pidgeon et al. | 436/161 |
| 2003/0113797 A1 * | 6/2003 | Jia et al. | 435/7.1 |
| 2004/0137420 A1 | 7/2004 | Yasuda et al. | |
| 2006/0147913 A1 | 7/2006 | Okamoto | |
| 2007/0020180 A1 | 1/2007 | Wang et al. | |

FOREIGN PATENT DOCUMENTS

KR 20090115930 A 11/2009

OTHER PUBLICATIONS

Eldridge et al. Analytical Chemistry, vol. 74, 2002, pp. 3963-3971.*
Park et al. Mass Spectrometry Letters, vol. 1, No. 1, Dec. 15, 2010, pp. 13-16.*
International Search Report & Written Opinion of the International Searching Authority; Application No. PCT/KR2010/008988; Issued: Sep. 9, 2011; Mailing Date: Sep. 14, 2011; 7 pages.

* cited by examiner

*Primary Examiner* — Maureen Wallenhorst
(74) *Attorney, Agent, or Firm* — St. Onge Steward Johnston & Reens LLC

(57) ABSTRACT

A method for discovering pharmacologically active substances from natural products at high speed, including: obtaining an activity profile by testing pharmacological activity of a plurality of samples; obtaining mass profiles based on mass spectra resulting from analysis of the samples by mass spectrometry; and determining molecular weight of pharmacologically active substances by comparing and analyzing the activity profile and the mass profile. The method allows fast discovery of pharmacologically active substances by performing high resolution mass spectrometry for numerous components included in an extract sample of natural products and comparing with the activity test data. The information about the intensity of the activity of the pharmacologically active substances of the natural products allows effective utilization of the natural products.

9 Claims, 4 Drawing Sheets

METHOD FOR DISCOVERING PHARMACOLOGICALLY ACTIVE SUBSTANCE OF NATURAL PRODUCTS USING HIGH RESOLUTION MASS SPECTROMETRY AND PHARMACOLOGICAL ACTIVITY TEST

CROSS-REFERENCE TO RELATED APPLICATIONS

The present application is a continuation of pending International patent application PCT/KR2010/008988 filed on Dec. 15, 2010 which designates the United States and claims priority from Korean patent application 10-2009-0133083 filed on Dec. 29, 2009, the content of which is incorporated herein by reference.

FIELD OF THE INVENTION

This disclosure relates to a method for discovering pharmacologically active substances from natural products.

BACKGROUND OF THE INVENTION

Extracts obtained from plant resources contain a lot of mixtures, in which various pharmacologically active substances are included. As exemplified by the analgesic aspirin, which was obtained from willow, and the anticancer drug taxol, which was obtained from the yew tree, plant extracts are a rich repository of pharmacologically active substances. At present, the most important two procedures in discovering pharmacologically active substances from plant extracts are separation of components and activity test. In order to analyze a plant extract, which is a very complex mixture, the individual components are separated through fractionation and separation to reduce the degree of mixing. Then, the fractions resulting from each fractionation step are subjected to activity test to select the fraction with the highest activity, which is further subjected to fractionation and activity test. This procedure is repeated to discover the effective components.

Since the fractions of the extract are still mixtures and the overall activity of the fraction mixture, not the activity of the individual components, is tested through the activity test, it is impossible to acquire information about specific components until the components are completely separated through the fractionation procedure. Thus, the desired substance can be obtained only after the time- and labor-consuming efforts of fractionation, separation and purification.

Thus, there is a need for reducing the time and efforts required for discovering desired substances by allowing the extraction of information about individual components in a mixture.

SUMMARY OF THE INVENTION

Technical Problem

This disclosure is directed to providing a method for discovering pharmacologically active substances from natural products by acquiring information about individual components from a plurality of samples through high resolution mass spectrometry, thereby reducing time and efforts required for discovering pharmacologically active substances.

Technical Solution

In one general aspect, there is provided a method for discovering pharmacologically active substances from natural products, including: obtaining an activity profile by testing pharmacological activity of a plurality of samples; obtaining mass profiles based on mass spectra resulting from analysis of the samples by mass spectrometry; and determining molecular weight of pharmacologically active substances by comparing and analyzing the activity profile and the mass profile.

In another general aspect, there is provided a method for discovering pharmacologically active substances from natural products, further including: determining molecular formula of the pharmacologically active substances based on the mass profile.

ADVANTAGEOUS EFFECTS

The method for discovering pharmacologically active substances from natural products according to the present disclosure is advantageous in that information about pharmacologically active substances in an extract of natural products or fractions thereof can be acquired and desired substances can be separated quickly by designing a more efficient separation scheme based on the information about the pharmacologically active substances.

Further, by providing information about intensity of activity of the discovered active substances, the present disclosure allows effective utilization of natural products.

BRIEF DESCRIPTION OF THE DRAWINGS

The above and other aspects, features and advantages of the disclosed exemplary embodiments will be more apparent from the following detailed description taken in conjunction with the accompanying drawings in which.

DETAILED DESCRIPTION OF THE INVENTION

Figure 1:
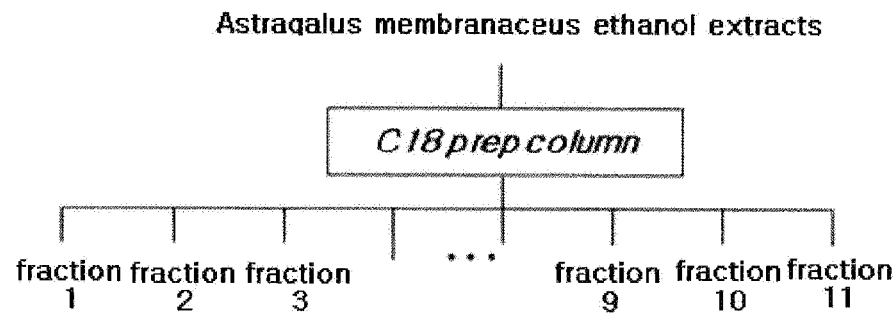
FIG. 1 illustrates fractionation of an *Astragalus membranaceus* extract into a plurality of fractions.

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein. Rather, these exemplary embodiments are provided so that this disclosure will be thorough and complete, and will fully convey the scope of this disclosure to those skilled in the art. In the description, details of well-known features and techniques may be omitted to avoid unnecessarily obscuring the presented embodiments.

The terminology used herein is for the purpose of describing particular embodiments only and is not intended to be limiting of this disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced item. The use of the terms "first", "second", and the like does not imply any particular order, but they are included to identify individual elements. Moreover, the use of the terms first, second, etc. does not denote any order or importance, but rather the terms first, second, etc. are used to distinguish one element from another. It will be further understood that the terms "comprise" and/or "comprising" or "includes" and/or "including" when used in this specification, specify the presence of stated features, regions, integers, steps, operations, elements, and/or , components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In an aspect, the present disclosure provides a method for discovering pharmacologically active substances from natural products, including: obtaining an activity profile by testing pharmacological activity of a plurality of samples; obtaining mass profiles based on mass spectra resulting from analysis of the samples by mass spectrometry; and determining molecular weight of pharmacologically active substances by comparing and analyzing the activity profile and the mass profile.

The sample may be any material from which pharmacologically active substances can be discovered, without particular limitation.

In an embodiment of the present disclosure, the sample may be a natural extract or a mixture thereof. The natural extract refers to an extract of natural products. As used herein, the natural product refers to a naturally occurring substance with no human intervention. The natural extract may be any extract of a natural product, without particular limitation. As non-limiting examples, it may be a plant extract, an animal extract, a microbial extract or a mineral extract.

In an embodiment of the present disclosure, the sample may be a fraction of a natural extract. Since the natural extract includes numerous compounds, a process of fractionating the extract into multiple fractions may precede for discovery of active components.

The method of fractionation may be one commonly used in the art and is not particularly limited. As non-limiting examples, one or more method(s) selected from a group consisting of chromatographic separation, liquid-liquid separation based on solubility difference, separation based on specific gravity difference, centrifugation based on density difference, solid phase extraction and separation based on color difference may be employed.

The chromatographic separation may be carried out by a chromatographic separation procedure commonly used in the art, without particular limitation. As non-limiting examples, one or more method(s) selected from a group consisting of high-performance liquid chromatography (HPLC), liquid chromatography, paper chromatography, ion-exchange chromatography, thin layer chromatography, partition chromatography, affinity chromatography, gas chromatography, adsorption chromatography and gel permeation chromatography may be employed.

In an embodiment of the present disclosure, when obtaining the activity profile, the test of pharmacological activity may comprise quantifying physiological activity regulating effect or preventive or therapeutic effect against diseases.

The physiological activity refers to an activity of promoting or inhibiting biological function of an organism, and the regulation of the physiological activity refers to correction of abnormal pathological conditions caused by deficiency or excessive secretion of regulatory substances. In the present disclosure, the pharmacological activity test may be any one capable of quantifying the physiological activity regulating effect, without particular limitation.

Further, the pharmacological activity test may be any one capable of quantifying the preventive or therapeutic effect against diseases, without particular limitation including the type of diseases.

As non-limiting examples, the pharmacological activity test may comprise one or more selected from antioxidant activity test, anticancer test, antiinflammatory test and antibacterial test.

In an embodiment of the present disclosure, the activity profile may be obtained as a result of the pharmacological activity test.

In an embodiment of the present disclosure, the mass profile may be obtained based on a mass spectrum resulting from measurement of molecular weight and abundance of components by high resolution mass spectrometry.

The most stable property of a molecule least affected by the change in neighboring environment is mass. Thus, mass spectrometry is the most frequently employed to analyze constituents of a complex compound. The mass spectrometry allows analysis of the constituents of a natural extract at once. Since accurate analysis may be difficult for a mixture sample because of superposition of mass spectrometry signals, a high resolution mass spectrometer capable of avoiding superposition of the signals may be used for the mass spectrometry.

High resolution mass spectrometric measurement of the natural extract or fraction allows the measurement of not only the molecular weight of individual components but also relative contents thereof on a single mass spectrum. This is called the mass profile of the fraction. From the mass profile, the contents of the individual components in each fraction may be measured.

Also, in an embodiment of the present disclosure, a single or a plurality of pharmacologically active substance(s) may be discovered by determining molecular weight of the pharmacologically active substance(s) from comparison and analysis of the mass profile and the activity profile.

An active component to be discovered from natural extracts may be included in a large amount in a natural extract exhibiting high activity and in a small amount in a natural extract exhibiting low activity. Similarly, an active component to be discovered from natural extracts may be included in a large amount in a fraction exhibiting high activity and in a small amount in a fraction exhibiting low activity. That is to say, the shape of the mass profile of the component coincides with that of the activity profile. Likewise, if there are a plurality of pharmacological active components, the shape of the mass profile of the components coincides with that of the activity profile.

The comparison and analysis of the activity profile and the mass profile may be performed by comparison of correlation coefficients, newly developed by the inventors.

The correlation coefficients newly designed by the inventors are represented by Equation 1:

$$C_j = \sum_{t=1}^{N} (a_k^0 \times m_{kj}^0) \quad \langle \text{Equation 1} \rangle$$

where j: j-th m/z bin when the mass spectrum is divided into bins with given mass intervals;

$a^0_k$: normalized activity of k-th fraction $m^0_{kj}$: normalized intensity of the mass peak of the k-th fraction at the j-th bin; and N: number of the fractions.

The normalized activity is obtained by dividing the fraction activity by a square root of the sum of squares of all fraction activities. The normalized intensity of the mass peak of the k-th fraction at the j-th bin is obtained by dividing the intensity of the peak by the sum of squares of all intensities at the j-th bin, as shown in Equation 2.

$$m^0_{kj} = m_{kj} / \{(m_{1j})^2 + (m_{2j})^2 + (m_{3j})^2 + \ldots + (m_{Nj})^2\}^{1/2} \quad \text{<Equation 2>}$$

When the correlation coefficient is maximum, the corresponding mass profile bin may be determined as the pharmacologically active component showing the most similar pattern as that of the activity profile.

Specifically, the molecular weight of the pharmacologically active substances may be determined by comparing and analyzing the activity profile and the mass profile as follows.

Suppose that a mass spectrum obtained from mass spectrometry of i-th fraction fi from among N fractions $\{f_1, f_2, f_3, f_N\}$ is divided into 1900 bins, at 1 Da intervals, from 100 Da to 2000 Da. The peak intensity at each bin may be represented by $\{m_{i1}, m_{i2}, m_{i3}, \ldots, m_{i1900}\}$, where $m_{ij}$ denotes the intensity of the mass peak satisfying m/z=(100+j) Da at the i-th fraction.

Let's define a vector $V_j = \{m_{1j}, m_{2j}, m_{3j}, \ldots, m_{Nj}\}$ (j=1, ..., 1900) as the mass profile value of the j-th bin. After normalizing 1901 vectors $\{A, V_1, V_2, V_3, \ldots, V_{1900}\}$, where $A = \{a_1, a_2, a_3, \ldots, a_N\}$, as in Equation 2, so that the maximum of $V_j$ becomes 1, and comparing the correlation coefficients, the mass bin having a higher correlation coefficient is selected as the mass bin exhibiting a more similar pattern to the activity.

The molecular weight of the pharmacologically active substance is determined with respect to the mass bin selected by performing the comparison and analysis of the activity profile and the mass profile through the comparison of correlation coefficients newly developed by the inventors.

Let's represent the normalized vectors of the activity profile vector and the mass bin intensity vector defined according to the comparison of correlation coefficients newly developed by the inventors as $A^0 = \{a^0_1, a^0_2, a^0_3, \ldots, a^0_N\}$ and $V_{0j} = \{m^0_{1j}, m^0_{2j}, m^0_{3j}, \ldots, m^0_{Nj}\}$, respectively. If the correlation coefficient between $A^0$ and $V^0_j$ is defined by Equation 1, the bin j having the maximum $C_j$ value is determined as the bin exhibiting the most similar pattern.

When determining the molecular weight of the pharmacologically active substances by comparing and analyzing the activity profile and the mass profile, the determination of the mass profile exhibiting the most similar pattern with the pharmacological activity profile among fractions having the same molecular weight may be performed using a clustering algorithm, as well as the comparison of correlation coefficients newly developed by the inventors.

The clustering algorithm may involve, as non-limiting examples, principal component analysis or support vector machine.

Use of the clustering algorithm such as the principal component analysis or support vector machine in addition to the comparison of correlation coefficients newly developed by the inventors may improve resolution and reduce analysis time in discovering effective pharmacologically active substances from natural products. Application of the clustering algorithm to the pharmacological activity and mass profile vectors $\{A, V_1, V_2, V_3, \ldots, V_{1900}\}$ allows determination of a group of mass profiles exhibiting a similar pattern with the pharmacological activity vector.

In an embodiment, the present disclosure may further comprise determining molecular formula of the pharmacologically active substances based on the mass profile.

Since high resolution mass spectrometry allows accurate measurement, molecular formula may be determined based on the molecular weight measurement of the individual components.

Because the mass profile contains information about the molecular weight and content of the plurality of compounds included in the natural extract or fraction, molecular formula can be determined based on the information of the mass profile of the pharmacologically active substances obtained from the comparison with the activity profile. Further, important information that allows the identification of the compound may be provided.

By providing information about the intensity of the activity of pharmacologically active substances included in natural products, the present disclosure may allow effective utilization of the natural products.

The examples and experiments will now be described. The following examples and experiments are for illustrative purposes only and not intended to limit the scope of this disclosure.

EXAMPLE 1

Fractionation of Natural Extract into Multiple Fractions

An ethanol extract of *Astragalus membranaceus* (200 g) was fractionated into 11 fractions by liquid chromatography. The stationary phase was fine $C_{18}$ particles packed in a column, and the mobile phase was distilled water and ethanol. The composition of the mobile phase was varied from 100% distilled water initially, for 10 minutes, to 100% ethanol over 100 minutes. The eluates were collected at 10 minute intervals to obtain 11 fractions (FIG. 1).

EXAMPLE 2

Preparation of Activity Profile 1,1-Diphenyl-2-picrylhydrazyl (DPPH) antioxidant activity test was carried out in order to evaluate antioxidant activity of each fraction. The antioxidant activity of scavenging free radicals may be evaluated by measuring the DPPH radical scavenging activity. First, 50% ethanol was added to the extract powder obtained by freeze-drying the 11 fractions to prepare 11 sample solutions (100 μg/mL, 1 mL). After diluting the 11 sample solutions 2-fold using ethanol, 60 μM DPPH solution (100 μL) was added to each sample solution. After waiting for 30 minutes, the quantity of DPPH scavenged from each sample solution was determined by measuring absorbance at 517 nm using a UV absorption detector.

Figure 2:
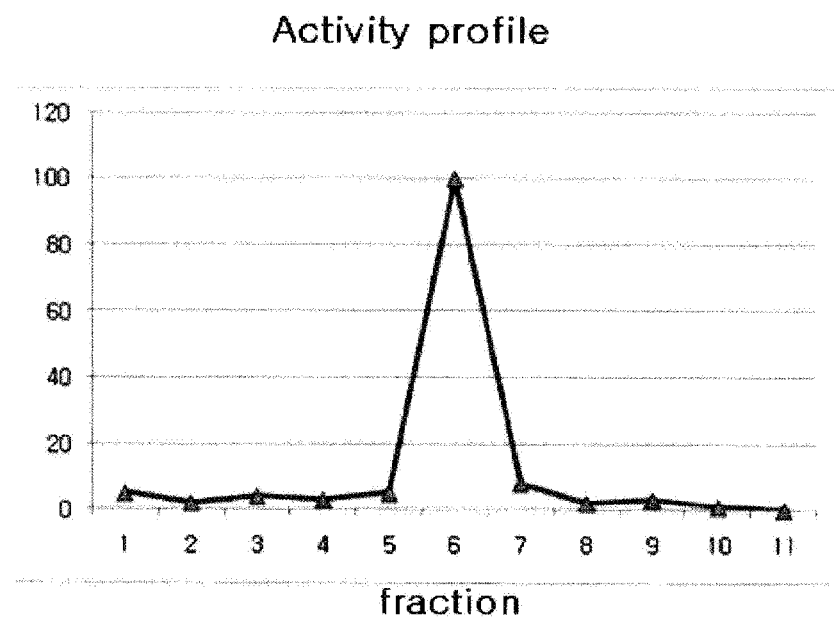
FIG. 2 shows an antioxidant activity profile prepared from antioxidant activity test of fractions.

Chlorogenic acid was used as standard for evaluation. The result is shown in Table 1 and FIG. 2.

TABLE 1

| Samples | Concentration | Inhibition (%) | Conversion factor |
|---|---|---|---|
| Chlorogenic acid | 25 µg/mL | 93.5 | 122.5 |
| Fraction 1 | Diluted 2-fold | 3.87 | 5.1 |
| Fraction 2 | Diluted 2-fold | 1.526 | 2.0 |
| Fraction 3 | Diluted 2-fold | 3.252 | 4.3 |
| Fraction 4 | Diluted 2-fold | 2.329 | 3.1 |
| Fraction 5 | Diluted 2-fold | 3.875 | 5.1 |
| Fraction 6 | Diluted 2-fold | 76.3 | 100.0 |
| Fraction 7 | Diluted 2-fold | 6.174 | 8.1 |
| Fraction 8 | Diluted 2-fold | 1.726 | 2.3 |
| Fraction 9 | Diluted 2-fold | 2.492 | 3.3 |
| Fraction 10 | Diluted 2-fold | 0.763 | 1.0 |
| Fraction 11 | Diluted 2-fold | 0.031 | 0.0 |
| (−)DPPH | | 100 | 131.1 |
| (+)DPPH | | 0 | 0.0 |

EXAMPLE 3

Preparation of Mass Profile

Mass spectrum of the 11 fractions was obtained using a high resolution mass spectrometer (Apex-Qe 15T FT-ICR MS: Bruker Daltonics). For each fraction, average mass resolution was 400,000, and average error was within 1 ppm.

Figure 3:
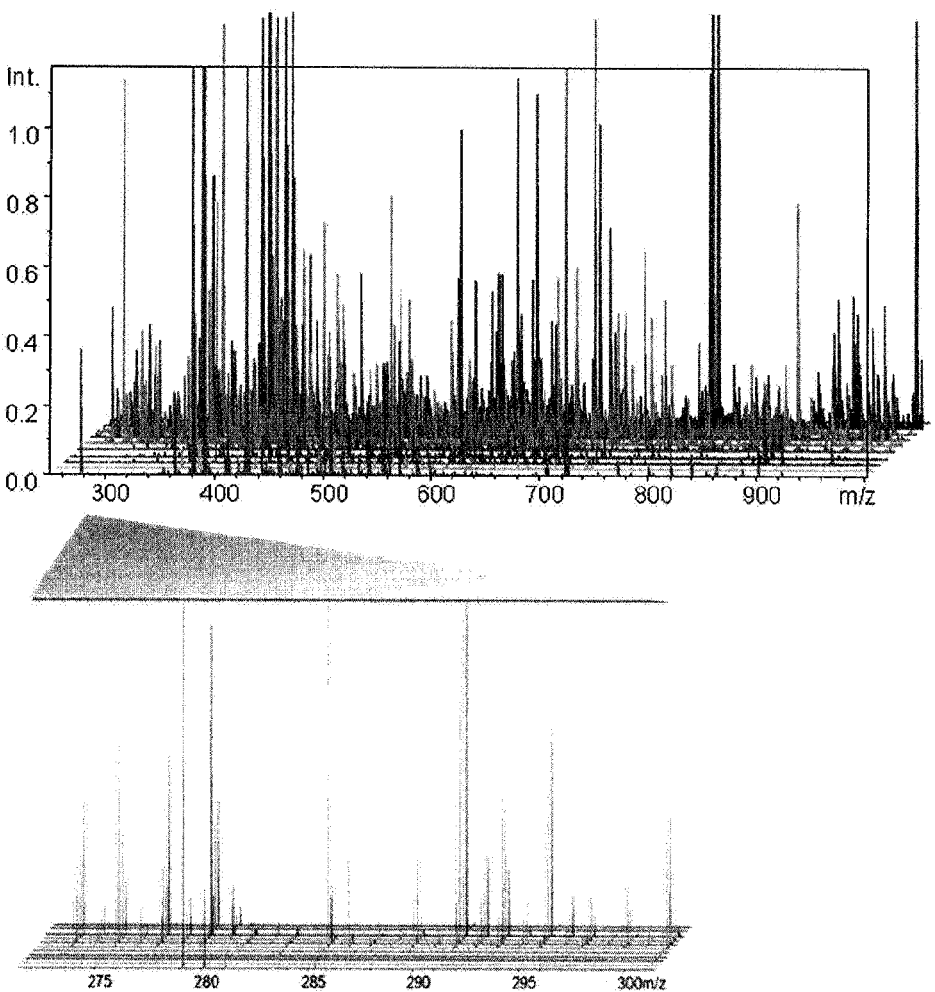
FIG. 3 shows mass spectra obtained from analysis of the components of fractions by high resolution mass spectrometry and an enlarged portion thereof, showing that the individual components can be analyzed without superimposition of signals.

Based on the mass spectrum, a mass profile exhibiting the molecular weight and relative content of the substances included in each fraction was obtained (FIG. 3).

EXAMPLE 4

Comparison and Analysis of Profiles

The mass spectrum of the i-th fraction $f_i$ of the 11 fractions $\{f_1, f_2, f_3, \ldots f_{11}\}$ obtained from the mass spectrometry was divided into 23 bins from 276.204 Da to 295.227 Da. The peak intensity at each bin was represented as $\{m_{i1}, m_{i2}, m_{i3}, \ldots, m_{i23}\}$, where $m_{ij}$ is the intensity of the j-th peak in an ascending order of m/z in the mass spectrum of the i-th fraction. And, a vector $V_j = \{m_{1j}, m_{2j}, m_{3j}, \ldots, m_{11j}\}$ (j=1, . . . , 23) was defined as the mass spectrometry profile value of the j-th bin.

After normalizing 23+1 vectors $\{A, V_1, V_2, V_3, \ldots, V_{23}\}$, where $A = \{a_1, a_2, a_3, \ldots, a_{11}\}$, the mass spectrum bin exhibiting a similar pattern to the activity was determined by the comparison of correlation coefficients newly developed by the inventors.

The normalized vectors of the activity profile vector and the mass bin intensity vector defined were represented as $A^0 = \{a^0_1, a^0_2, a^0_3, \ldots, a^0_{11}\}$ and $V^0_j = \{m^0_{1j}, m^0_{2j}, m^0_{3j}, \ldots, m^0_{11j}\}$, respectively. The correlation coefficient between $A^0$ and $V^0_j$ was defined as $$C_j = \sum_{t=1}^{N}(a^0_k \times m^0_{kj}), \; N = 11$$

The bin j having the maximum $C_j$ value was determined as the bin exhibiting the most similar pattern.

The total number of the bins was 23, with more than one peaks detected for each fraction. The $C_j$ values are given in Table 2.

TABLE 2

| | $m^°_{ij}$ | | | | | | | | | | | |
|---|---|---|---|---|---|---|---|---|---|---|---|---|
| m/z | fraction 1 | fraction 2 | fraction 3 | fraction 4 | fraction 5 | fraction 6 | fraction 7 | fraction 8 | fraction 9 | fraction 10 | fraction 11 | $C_j$ |
| 276.204 | 0.00 | 0.00 | 0.00 | 0.00 | 0.00 | 0.32 | 0.82 | 0.41 | 0.25 | 0.00 | 0.00 | 30.78 |
| 277.180 | 0.00 | 0.00 | 0.00 | 0.00 | 0.00 | 0.66 | 0.75 | 0.00 | 0.00 | 0.00 | 0.00 | 55.19 |
| 277.217 | 0.00 | 0.00 | 0.00 | 0.00 | 0.00 | 0.03 | 0.23 | 0.64 | 0.73 | 0.00 | 0.00 | 6.36 |
| 279.157 | 0.00 | 0.00 | 0.00 | 0.00 | 0.00 | 0.81 | 0.00 | 0.00 | 0.00 | 0.39 | 0.43 | 62.18 |
| 279.160 | 0.82 | 0.00 | 0.00 | 0.00 | 0.00 | 0.00 | 0.00 | 0.02 | 0.50 | 0.17 | 0.20 | 4.60 |
| 283.154 | 0.00 | 0.00 | 0.00 | 0.00 | 0.00 | 0.61 | 0.52 | 0.00 | 0.60 | 0.00 | 0.00 | 51.39 |
| 285.076 | 0.00 | 0.00 | 0.00 | 0.00 | 0.00 | 1.00 | 0.02 | 0.00 | 0.00 | 0.00 | 0.00 | 76.43 |
| 285.170 | 0.00 | 0.00 | 0.00 | 0.00 | 0.00 | 0.78 | 0.63 | 0.00 | 0.00 | 0.00 | 0.00 | 63.08 |
| 286.076 | 0.00 | 0.00 | 0.00 | 0.00 | 0.00 | 1.00 | 0.03 | 0.00 | 0.00 | 0.00 | 0.00 | 76.47 |
| 289.175 | 0.00 | 0.00 | 0.00 | 0.00 | 0.00 | 0.48 | 0.88 | 0.00 | 0.00 | 0.00 | 0.00 | 41.85 |
| 289.180 | 0.00 | 0.00 | 0.00 | 0.00 | 0.00 | 0.51 | 0.83 | 0.24 | 0.06 | 0.00 | 0.00 | 44.42 |
| 290.183 | 0.00 | 0.00 | 0.00 | 0.00 | 0.00 | 0.53 | 0.82 | 0.23 | 0.00 | 0.00 | 0.00 | 45.80 |
| 291.190 | 0.00 | 0.00 | 0.00 | 0.00 | 0.00 | 0.17 | 0.29 | 0.50 | 0.80 | 0.00 | 0.00 | 17.24 |
| 291.193 | 0.00 | 0.00 | 0.00 | 0.00 | 0.00 | 0.55 | 0.83 | 0.00 | 0.00 | 0.00 | 0.00 | 47.44 |
| 291.196 | 0.00 | 0.00 | 0.00 | 0.00 | 0.00 | 0.23 | 0.38 | 0.63 | 0.64 | 0.00 | 0.00 | 22.43 |
| 292.199 | 0.00 | 0.00 | 0.00 | 0.00 | 0.00 | 0.18 | 0.30 | 0.67 | 0.66 | 0.00 | 0.00 | 18.52 |
| 293.175 | 0.00 | 0.00 | 0.00 | 0.00 | 0.00 | 0.56 | 0.59 | 0.59 | 0.00 | 0.00 | 0.00 | 47.30 |
| 293.211 | 0.00 | 0.00 | 0.00 | 0.00 | 0.00 | 0.15 | 0.59 | 0.75 | 0.26 | 0.00 | 0.00 | 16.71 |
| 293.284 | 0.00 | 0.00 | 0.00 | 0.00 | 0.00 | 0.53 | 0.85 | 0.00 | 0.00 | 0.00 | 0.00 | 45.33 |
| 294.215 | 0.00 | 0.00 | 0.00 | 0.00 | 0.00 | 0.18 | 0.58 | 0.76 | 0.24 | 0.00 | 0.00 | 18.97 |
| 295.152 | 0.00 | 0.00 | 0.00 | 0.00 | 0.00 | 0.80 | 0.60 | 0.00 | 0.00 | 0.00 | 0.00 | 64.98 |
| 295.191 | 0.00 | 0.00 | 0.00 | 0.00 | 0.00 | 0.42 | 0.91 | 0.00 | 0.00 | 0.00 | 0.00 | 37.33 |
| 295.277 | 0.00 | 0.00 | 0.00 | 0.00 | 0.00 | 0.03 | 0.40 | 0.53 | 0.75 | 0.00 | 0.01 | 7.37 |
| $A^°_{ij}$ | 3.87 | 1.53 | 3.25 | 2.33 | 3.88 | 76.3 | 6.17 | 1.73 | 2.49 | 0.76 | 0.03 | |

As seen from Table 2, the component with a molecular weight of 285.0755 and its isotopic component with a molecular weight of 286.0762 were discovered as the active components showing the largest $C_j$ value. The accuracy was so high as to detect the isotopic peak.

Figure 4:
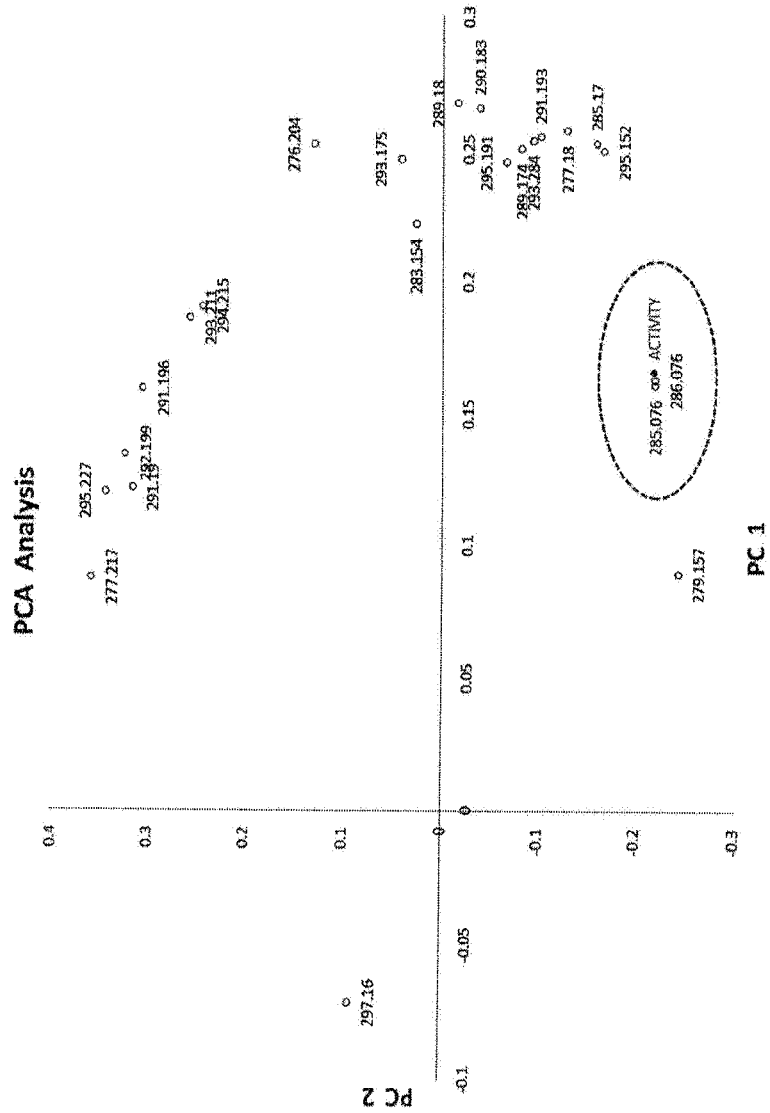
FIG. 4 shows a result of principal component analysis using normalized measurement values (It can be seen that the molecular weights of the active components with a pattern similar to the activity profile are 285.076 Da and 286.076 Da.)

Principal component analysis was carried out on the normalized values given in Table 2. The result is shown in FIG. 4. As seen from FIG. 4, the mass value with a higher correlation, i.e. more similar pattern to the activity profile, can be easily determined by selecting the mass bin vector closer to the activity vector.

EXAMPLE 5

Figure 5:
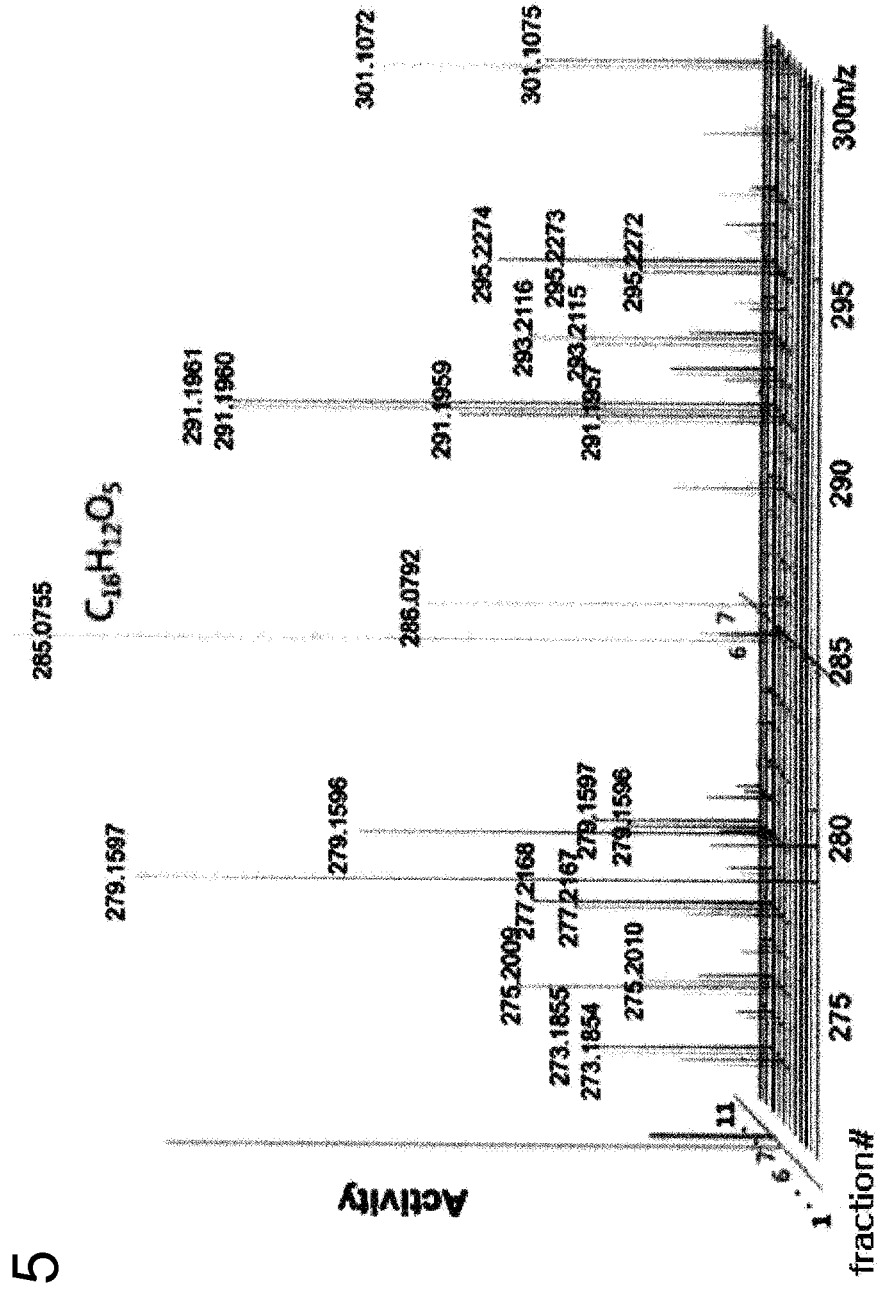
FIG. 5 shows a result of directly comparing and analyzing the antioxidant activity profile of FIG. 2 and the mass profile of FIG. 3 on the same graph.

Determination of Molecular Formula and Identification of Pharmacologically Active Substance The component with a molecular weight of 285.0755 was determined as the active component exhibiting the same pattern as the activity profile. The component molecular formula could be easily identified as $C_{16}H_{12}O_5$. (FIG. 5).

While the exemplary embodiments have been shown and described, it will be understood by those skilled in the art that various changes in form and details may be made thereto without departing from the spirit and scope of this disclosure as defined by the appended claims.

In addition, many modifications can be made to adapt a particular situation or material to the teachings of this disclosure without departing from the essential scope thereof. Therefore, it is intended that this disclosure not be limited to the particular exemplary embodiments disclosed as the best mode contemplated for carrying out this disclosure, but that this disclosure will include all embodiments falling within the scope of the appended claims.

What is claimed is:

1. A method for discovering pharmacologically active substances from natural products, comprising:
   obtaining an activity profile by testing pharmacological activity of a plurality of samples which are natural products extracts, mixture thereof, or fractions of the natural products extracts;
   obtaining mass profiles based on mass spectra resulting from analysis of the samples by mass spectrometry; and
   determining molecular weight of pharmacologically active substances by comparing and analyzing the activity profile and the mass profile performed by comparison of correlation coefficients represented by Equation 1:

$$C_j = \sum_{t=1}^{N} (a_k^0 \times m_{kj}^0) \quad \langle \text{Equation 1} \rangle$$

where
j: j-th bin when the mass spectra is divided into bins with given mass intervals;
$a^0_k$: normalized activity of k-th sample;
$m^0_{kj}$: normalized intensity of a mass peak of he k-th sample at the j-th bin; and
N: number of the samples.

2. The method for discovering pharmacologically active substances from natural products according to claim 1, further comprising:
   determining molecular formula of the pharmacologically active substances based on the mass profile.

3. The method for discovering pharmacologically active substances from natural products according to claim 1, wherein the fraction is obtained from fractionation using one or more method(s) selected from a group consisting of chromatographic separation, liquid-liquid separation based on solubility difference, separation based on specific gravity difference, centrifugation based on density difference, solid phase extraction (SPE) and separation based on color difference.

4. The method for discovering pharmacologically active substances from natural products according to claim 3, wherein the chromatographic separation employs one or more method(s) selected from a group consisting of high-performance liquid chromatography (HPLC), liquid chromatography, paper chromatography, ion-exchange chromatography, thin layer chromatography, partition chromatography, affinity chromatography, gas chromatography, adsorption chromatography and gel permeation chromatography.

5. The method for discovering pharmacologically active substances from natural products according to claim 1, wherein, in said determining the molecular weight, the comparison and analysis of the activity profile and the mass profile are carried out using a clustering algorithm.

6. The method for discovering pharmacologically active substances from natural products according to claim 5, wherein the clustering algorithm involves principal component analysis or support vector machine.

7. The method for discovering pharmacologically active substances from natural products according to claim 1, wherein, in said obtaining the activity profile, the test of pharmacological activity comprises quantifying physiological activity regulating effect or preventive and therapeutic effect against diseases.

8. The method for discovering pharmacologically active substances from natural products according to claim 1, wherein, in said obtaining the activity profile, the test of pharmacological activity comprises one or more selected from antioxidant activity test, anticancer test, antiinflammatory test and antibacterial test.

9. The method for discovering pharmacologically active substances from natural products according to claim 1, wherein, in said obtaining the mass profiles, the mass profiles are obtained based on mass spectra resulting from measurement of molecular weight and abundance of components by high resolution mass spectrometry.

* * * * *